US009387056B2

(12) United States Patent
Wachter et al.

(10) Patent No.: US 9,387,056 B2
(45) Date of Patent: Jul. 12, 2016

(54) PROCESS FOR PRODUCING A DENTAL SHAPED PART BY STEREOLITHOGRAPHY

(71) Applicants: Ivoclar Vivadent AG, Schaan (LI); Technische Universitat Wien, Vienna (AT)

(72) Inventors: Wolfgang Wachter, Schaan (LI); Jörg Ebert, Buchs (CH); Dieter Voser, Schaan (LI); Norbert Moszner, Mauren (LI); Volker Rheinberger, Vaduz (LI); Jürgen Stampfl, Vienna (AT)

(73) Assignees: Ivoclar Vivadent AG, Schaan (LI); Technische Universitat Wien, Vienna (AT)

( * ) Notice: Subject to any disclaimer, the term of this patent is extended or adjusted under 35 U.S.C. 154(b) by 0 days.

(21) Appl. No.: 14/391,524

(22) PCT Filed: Apr. 11, 2013

(86) PCT No.: PCT/EP2013/057635
§ 371 (c)(1),
(2) Date: Oct. 9, 2014

(87) PCT Pub. No.: WO2013/153183
PCT Pub. Date: Oct. 17, 2013

(65) Prior Publication Data
US 2015/0111176 A1 Apr. 23, 2015

(30) Foreign Application Priority Data
Apr. 11, 2012 (EP) ..................................... 12163824

(51) Int. Cl.
*A61C 5/08* (2006.01)
*A61C 13/00* (2006.01)
(Continued)

(52) U.S. Cl.
CPC .............. *A61C 13/0013* (2013.01); *A61C 5/10* (2013.01); *A61C 13/082* (2013.01); *A61C 13/26* (2013.01);
(Continued)

(58) Field of Classification Search
CPC ........ A61C 5/08; A61C 5/10; A61C 13/0013; B29C 67/0066
USPC ................... 264/401; 433/218, 219, 223, 226
See application file for complete search history.

(56) References Cited

U.S. PATENT DOCUMENTS 5,768,134 A 6/1998 Swaelens et al.
6,043,361 A 3/2000 Evans et al.
(Continued)

FOREIGN PATENT DOCUMENTS

CA 2296227 A1 7/2000
CA 2371357 A1 9/2002
(Continued)

OTHER PUBLICATIONS

Lee, J.H. et al., Cure depth in photopolymerization: Experiments and theory, J. Mater. Res., vol. 16, No. 12, Dec. 2001; pp. 3536-3544.
(Continued)

*Primary Examiner* — Leo B Tentoni
(74) *Attorney, Agent, or Firm* — Ann M. Knab; Thad McMurray

(57) ABSTRACT

The invention relates to the use of a composite resin composition comprising
(a) at least one polyreactive binder,
(b) a first photopolymerization initiator having an absorption maximum at a wavelength of less than 400 nm,
(c) a second photopolymerization initiator having an absorption maximum at a wavelength of at least 400 nm and
(d) an absorber having an absorption maximum at a wavelength of less than 400 nm,
for the stereolithographic production of a dental shaped part based on composite resin.
The invention also relates to a process for the stereolithographic production of a dental shaped part and the use of the composite resin composition in this process.

37 Claims, 1 Drawing Sheet

(51) Int. Cl.
| | |
|---|---|
| B29C 67/00 | (2006.01) |
| G03F 7/00 | (2006.01) |
| G03F 7/027 | (2006.01) |
| G03F 7/029 | (2006.01) |
| A61C 5/10 | (2006.01) |
| A61K 6/00 | (2006.01) |
| A61C 13/08 | (2006.01) |
| A61C 13/271 | (2006.01) |
| B33Y 10/00 | (2015.01) |

(52) U.S. Cl.
CPC ........... *A61K 6/0052* (2013.01); *B29C 67/0066* (2013.01); *G03F 7/0037* (2013.01); *G03F 7/027* (2013.01); *G03F 7/029* (2013.01); *B33Y 10/00* (2014.12)

(56) References Cited

U.S. PATENT DOCUMENTS

| | | | |
|---|---|---|---|
| 6,344,556 | B1 | 2/2002 | Evans et al. |
| 6,479,592 | B2 | 11/2002 | Rheinberger et al. |
| 2001/0012596 | A1* | 8/2001 | Kunimoto et al. ........ 264/401 X |
| 2002/0143118 | A1 | 10/2002 | Rheinberger et al. |
| 2004/0077882 | A1 | 4/2004 | Moszner et al. |
| 2004/0235981 | A1* | 11/2004 | Qian ............................ 523/115 |
| 2007/0026509 | A1 | 2/2007 | Rogers et al. |
| 2007/0259309 | A1* | 11/2007 | West et al. ...................... 433/29 |
| 2009/0004579 | A1 | 1/2009 | Sarmah et al. |
| 2009/0148813 | A1 | 6/2009 | Sun et al. |
| 2010/0029801 | A1* | 2/2010 | Moszner et al. ............. 522/167 |
| 2015/0080490 | A1 | 3/2015 | Burtscher et al. |
| 2015/0111176 | A1 | 4/2015 | Wachter et al. |

FOREIGN PATENT DOCUMENTS

| | | |
|---|---|---|
| DE | 19938463 A1 | 2/2001 |
| DE | 19950284 A1 | 4/2001 |
| DE | 19903177 A1 | 7/2001 |
| DE | 10114290 A1 | 10/2002 |
| EP | 1413569 A1 | 4/2004 |
| EP | 2649981 A1 | 10/2013 |
| WO | 95/28688 A1 | 10/1995 |
| WO | 97/29901 A1 | 8/1997 |
| WO | 9729901 A1 | 8/1997 |
| WO | 01/12679 A1 | 2/2001 |
| WO | 0112679 A1 | 2/2001 |
| WO | 2004/108799 A1 | 12/2004 |
| WO | 2009/032228 A2 | 3/2009 |

OTHER PUBLICATIONS

Beil, A., Production of micro-components by stereolithography, Fortschr.-Ber. VDI, Reihe 2, Nr. 617, VDI Verlag Düsseldorf 2002, ISBN 3-18-361702-1, pp. 3 et seq.

Gebhardt, A., Vision of Rapid Prototyping, Ber. DGK 2006, vol. 83, No. 13, pp. 7-12.

Gebhardt, A., Additive Manufacturing Systems for Rapid Prototyping, Direct Tooling and Direct Manufacturing, 3. Aufl., Carl Hanser Verlag, München 2007, ISBN 978-3-446-22666-1, pp. 77 et seq.

Mesaric, E. et al., Diagnostic and temporary restorations using additive manufacturing from light-curing composite, Quintessenz Zahntech 2009, vol. 35, No. 9, pp. 1144-1153.

Spectra Group Limited, H-Nu Visible Light & Infrared Photoinitiators, Jul. 15, 2010, http://www.sglinc.com/photoin.htm.

Mahn, E., Clinical criteria for the successful curing of composites, Zahnmedizin 2011, vol. 101, No. 4, pp. 50-29.

Prahl, S., Anthraquinone, Oregon Medical Laser Center, Mar. 5, 2012, http://omlc.ogi.edu/spectra/PhotochemCAD/html/034.html.

Spectra Group Limited, Inc., H-Nu Visible Light & Infrared Photoinitiators, Jul. 15, 2010, pp. 1-6. http://www.sglinc.com/photoin.htm.

Prahl, S., Amnthraquinone, Oregon Medical Laser Center, Mar. 5, 2012, pp. 1-2. http://omlc.ogi.edu/spectra/PhotochemCAD/html/034.html.

Lee, J.H., et al., Cure depth in photopolymerization: Experiments and theory, J. Mater. Res., Dec. 2001, vol. 16, No. 12, pp. 3536-3544.

Gebhardt, A., Vision Rapid Prototyping, Generative Manufacturing of Ceramic Parts—A Survey, Plenary Lecture of the DKG-Symposium, vol. 83, No. 13, Nov. 29, 2005, pp. 7-12.

* cited by examiner (A)  (B)  (C)  (D)

PROCESS FOR PRODUCING A DENTAL SHAPED PART BY STEREOLITHOGRAPHY

CROSS-REFERENCE TO RELATED APPLICATIONS

This application is a National Stage application of International patent application PCT/EP2013/057635 filed on Apr. 11, 2013, which claims priority to European patent application No. 12163824.1 filed on Apr. 11, 2012, the disclosures of which are incorporated herein by reference in their entirety.

The present invention relates to the use of a composite resin composition as well as a process for the stereolithographic production of dental component parts such as inlays, onlays, crowns and bridges based on composite resin.

The term "rapid prototyping" (RP) covers generative manufacturing processes in which 3-dimensional models or component parts are produced from computer-aided design data (CAD data) (A. Gebhardt, Vision of Rapid Prototyping, Ber. DGK 83 (2006) 7-12). These are processes such as stereolithography (SL), selective laser sintering (SLS), 3D printing, fused deposition modelling (FDM), ink-jet printing (IJP), 3D plotting, multi-jet modelling (MJM), solid freeform fabrication (SFF), laminated object manufacturing (LOM), laser powder forming (LPF) and direct ceramic jet printing (DCJP), with which models, component parts or shaped parts can be produced cheaply even on a small scale (A. Gebhardt, Generative Fertigungs-verfahren, 3rd edition, Carl Hanser Verlag, Munich 2007, 77 et seq.). Stereolithography involves RP processes (A. Beil, Fertigung von Mikro-Bauteilen mittels Stereolithographie, Düsseldorf 2002, VDI-Verlag 3 et seq.) in which a shaped part is constructed in layers from a liquid and curable monomer resin on the basis of CAD data.

Nowadays, inlays, onlays and temporary prostheses based on composite resins are usually ground from blanks (industrially prefabricated blocks or discs) and then cemented in. However, the cementing of these polymer materials which are highly crosslinked on the surface requires quite a lot of effort, as the weakly reactive composite surface must be conditioned for a reliable adhesion to the tooth, for example by sandblasting, conditioning with primers, etc.

Stereolithographic processes for producing dental shaped bodies based on composite resins are also known per se (cf. Mesaric, Witkowski, Quintessenz Zahntech 2009, 35(9), 1144-1153). Stereolithographic production is highly advantageous in particular for producing dental component parts, because the molding and casting processes and/or the grinding and milling operations, which involve considerable manual outlay in the dental laboratory, can thus be greatly simplified and at the same time the large material loss which occurs with non-generative processes can be avoided. As a complete digital process chain is in place today, the standard process steps for producing for example multi-unit bridge frameworks (alignment in the articulator, wax modulation, embedding and casting) can be replaced by the digitization of the model, virtual design of the dental shaped body and its generative stereolithographic production.

A stereolithographic process for producing dental implants is known from WO 95/28688.

WO 97/29901 A1 describes a process and an apparatus for producing 3-dimensional parts from a liquid, curable medium. The parts are constructed in layers by tracing each individual layer with a laser and curing it. The next layer of curable material is then deposited by means of a scraper and subsequently likewise cured.

Compositions which are curable using visible light and their use for producing dental restorations from plastic materials with RP processes are described in DE 199 38 463 A1 and DE 199 50 284 A1. However, these often fail to achieve the precision desirable for dental component parts.

DE 101 14 290 A1 describes the production of dental shaped parts by 3D plotting using filled or unfilled materials that are meltable, condensable and curable thermally or with visible or in particular with UV light.

Stereolithographic processes for the production of dental component parts usually use light having wavelengths in the UV range as well as corresponding photoinitiators. In addition, UV absorbers are often also used, which reduce irradiation and scattering effects during the construction process and thus are intended to improve the precision of the component parts. However, stereolithographic systems which produce aesthetic, tooth-colored dental restorations with sufficient precision in the wavelength range of visible light are not known.

During the layered construction of dental component parts by means of stereolithographic processes, as a rule the polymerizable groups are only partially converted, with the result that the obtained component parts have a not yet fully formed strength and hardness. These component parts must therefore be post-cured in a further step after stereolithographic production and cleaning. This is carried out for example by irradiation and/or heat treatment. Here, the not yet converted available polymerizable groups react and thus lead to increased strength and hardness. However, this step also means that the surface inhibition layer of the component is reduced, which can have a negative effect on the adhesion to a cement or adhesive system.

In addition, the absorbers used often hinder the desired depth effect during photochemical post-curing. A good depth of cure is of central importance for the clinical performance of dental component parts based on composite resins. According to ISO 4049-2009 ("Dentistry—Polymer-based restorative materials"), the depth of cure is determined such that a cylindrical composite test piece is irradiated in a steel mould for the recommended time. The test piece is then taken out of the mould and the non-polymerized composite is removed with a plastic spatula. The height of the remaining cylinder, divided by 2, is defined as the depth of cure and is effectively a measure for how efficiently the composite can be cured by the irradiated light.

The depth of cure is dependent both on the process parameters and on the material properties. Thus, there is e.g. a logarithmic correlation between depth of cure and the intensity of the irradiated light and the exposure time, respectively (cf. J. H. Lee, R. K. Prud'homme, I. A. Aksay, J. Mater. Res. 16 (2001) 3536-3544). In this context, the emission spectrum of the radiation source should closely correspond to the absorption spectrum of the photoinitiator. Furthermore, the depth of cure correlates with the translucence of the composite, which in turn is influenced by, among other things, the refractive index of the resin matrix and the fillers, by the size of the filler particles as well as the type and concentration of the dyes added (E. Mahn, Zahnmedizin 2011, 50-59). The depth of cure is furthermore influenced by the type and concentration of the photoinitiator system, wherein mono-molecular photoinitiators are easier to control than bimolecular photoinitiator systems.

The object of the invention is to avoid the named disadvantages and to provide a process for producing dental component parts based on composite resins by means of stereolithography, which is characterized by high component accuracy, good curing depth and good mechanical and aesthetic properties of the dental component parts and allows for an optimum bonding to a tooth. In particular a process is to be provided wherein these advantageous results are achieved with low complexity of the equipment and as few work steps as possible.

This object is achieved according to the invention by the use of a composite resin composition comprising
(a) at least one polyreactive binder,
(b) a first photopolymerization initiator having an absorption maximum at a wavelength of less than 400 nm,
(c) a second photopolymerization initiator having an absorption maximum at a wavelength of at least 400 nm, and
(d) an absorber having an absorption maximum at a wavelength of less than 400 nm,
for the stereolithographic production of a dental shaped part based on composite resin.

Figure 1:
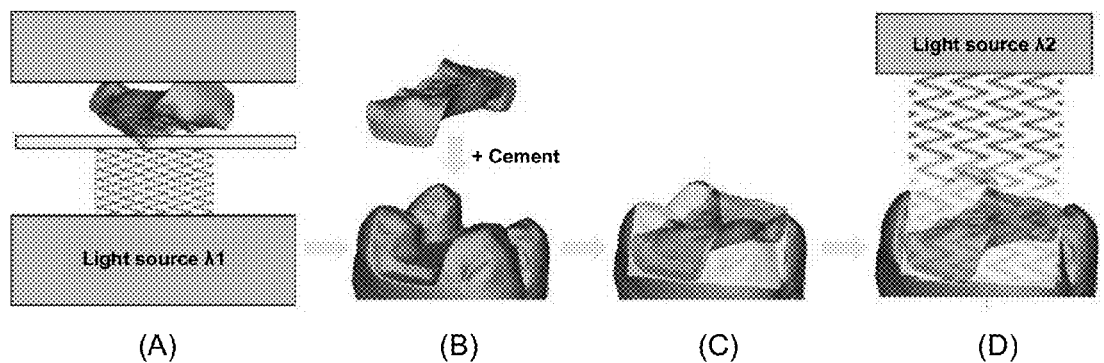
FIG. 1 shows a schematic diagram of a procedure in accordance with the invention.

According to the invention, the composite resin composition generally comprises a first photopolymerization initiator for the UV range, a second photopolymerization initiator for the visible range and a UV absorber. It was surprisingly found that the use of a composite resin composition according to the invention allows for the stereolithographic production of dental component parts based on composite resins with excellent precision, optimum curing depth and very good mechanical properties even in deeper layers.

The determination of the wavelength of the absorption maximum and of the molar absorption coefficient of the photoinitiators and absorbers is usually carried out by means of UV-VIS spectroscopy at room temperature using a solution of the relevant substance in a suitable solvent such as acetonitrile. The determination is preferably carried out using solutions having a concentration of 1 mM. A customary double-beam UV-VIS spectrometer can for instance be used for the measurement.

The longest-wavelength absorption maximum of the first photopolymerization initiator preferably is at a wavelength of less than 400 nm, in particular in the range of from 300 to less than 400 nm, preferably in the range of from 330 to less than 400 nm, particularly preferably in the range of from 345 to less than 400 nm and most preferably in the range of from 360 to less than 400 nm. The longest-wavelengh absorption maximum of the second photopolymerization initiator preferably is at a wavelength of at least 400 nm, in particular in the range of from 400 to 600 nm, particularly preferably in the range of from 400 to 500 nm and most preferably in the range of from 420 to 480 nm.

The absorption spectra of the first and second photopolymerization initiators can overlap to a certain extent. The difference between the longest-wavelength absorption maxima of the first and second photopolymerization initiator is preferably at least 5 nm, in particular at least 10 nm, most preferably at least 15 nm. It is further preferred that the first photopolymerization initiator has a molar decadic absorption coefficient of less than 10 l/(mol·cm) in the wavelength range of from 420 to 750 nm and in particular in the wavelength range of from 440 to 700 nm.

Phosphine oxides, benzoins, benzil ketals, acetophenones, benzophenones, thioxanthones as well as mixtures thereof are suitable in particular as first photopolymerization initiator used according to the invention.

Acyl- and bisacylphosphine oxides such as 2,4,6-trimethylbenzoyl diphenylphosphine oxide or bis-(2,4,6-trimethylbenzoyl)phenylphosphine oxide, benzoin, benzoin alkyl ether, benzil dialkyl ketals such as benzyl dimethyl ketal, α-hydroxyacetophenones such as 1-hydroxycyclohexyl-phenyl-ketone, 2-hydroxy-2-methyl-1-phenyl-1-propanone or 2-hydroxy-1-[4-(2-hydroxyethoxy)-phenyl]-2-methyl-1-propanone, α-dialkoxyacetophenones, α-aminoacetophenones such as 2-benzyl-2-(dimethylamino)-1-[4-(4-morpholinyl)-phenyl]-1-butanone or 2-methyl-1-[4-(methylthio)-phenyl]-2-(4-morpholinyl)-1-propanone, alkylthioxanthones such as i-propylthioxanthone as well as mixtures thereof are particularly suitable. Acyl- and bisacylphosphine oxides and in particular 2,4,6-trimethylbenzoyl diphenylphosphine oxide, bis-(2,4,6-trimethylbenzoyl)phenylphosphine oxide and their mixtures are particularly preferred.

α-Diketones, acylgermanium compounds, metallocenes and mixtures thereof are suitable in particular as second photopolymerization initiator used according to the invention.

α-Diketones such as camphorquinone, 9,10-phenanthrenequinone, 1-phenyl-propane-1,2-dione, diacetyl, 4,4'-dichlorobenzil or their derivatives, monoacyl- and diacylgermanium compounds such as benzoyltrimethylgermanium, dibenzoyldiethylgermanium or bis-(4-methoxybenzoyl)-diethylgermanium, titanocenes such as bis-($\eta^5$-2,4-cyclopentadien-1-yl)-bis-[2,6-difluoro-3-(1H-pyrrol-1-yl)phenyl]-titanium as well as mixtures thereof are particularly suitable. α-Diketones and in particular camphorquinone, 1-phenylpropane-1,2-dione and their mixtures are particularly preferred. Monoacyltrialkyl- and diacyldialkylgermanium compounds and in particular benzoyltrimethylgermanium, dibenzoyldiethylgermanium, bis-(4-methoxybenzoyl)-diethylgermanium and their mixtures are likewise particularly preferred. Mixtures of at least one α-diketone and at least one acylgermanium compound are also quite particularly preferred.

α-Diketones are preferably used in combination with amine accelerators. Tertiary amines are usually used as amine accelerators. Tertiary aromatic amines such as N,N-dialkylanilines, N,N-dialkyl-p-toluidines or N,N-dialkyl-3,5-xylidines, p-(N,N-dialkylamino)-phenylethanols, p-(N,N-dialkylamino)-benzoic acid derivatives, p-(N,N-dialkylamino)-benzaldehydes, p-(N,N-dialkylamino)-phenylacetic acid esters or p-(N,N-dialkylamino)-phenylpropionic acid esters are particularly suitable. Specific examples are N,N-dimethylaniline, N,N-dimethyl-p-toluidine, 3,5,N,N-tetramethylaniline, p-(N,N-dimethylamino)-benzaldehyde, p-(dimethylamino)-benzoic acid ethyl ester and p-(dimethylamino)-benzonitrile as well as mixtures thereof. Tertiary aliphatic amines such as tri-n-butylamine, 2-dimethylamino-ethanol, triethanolamine, dimethylaminoethyl methacrylate, N,N-dimethylbenzylamine, heterocyclic amines such as 1,2,2,6,6-penta-methylpiperidine, amino acid derivatives such as N-phenylglycine as well as mixtures thereof are also suitable. p-(Dimethylamino)-benzoic acid ethyl ester, dimethylaminoethyl methacrylate, N,N-dimethylaniline, N,N-dimethyl-p-toluidine, triethanolamine and their mixtures are particularly preferred. In particular such photopolymerization initiators are preferred which bleach out upon introduction of radiation the emission maximum of which is at a wavelength of at least 400 nm and thus no longer have undesirable inherent coloration after further curing. This applies in particular to the named acylgermanium compounds.

In a preferred embodiment, a mixture of at least one germanium compound with at least one α-diketone in combination with at least one amine accelerator is used as second photopolymerization initiator. Quite particularly preferred combinations of these photopolymerization initiators are described in parallel application EP 12163823.3.

The composite resin composition used according to the invention furthermore preferably comprises at least one absorber the longest-wavelength absorption maximum of which is at a wavelength of less than 400 nm, in particular in the range of from 300 to less than 400 nm, preferably in the range of from 330 to less than 400 nm, particularly preferably in the range of from 345 to less than 400 nm and most preferably in the range of from 360 to less than 400 nm. Benzotriazoles, triazines, benzophenones, cyanoacrylates, salicylic acid derivatives, hindered amine light stabilizers (HALS) as well as mixtures thereof are particularly suitable as absorbers. Inorganic salts such as nanoscale titanium dioxides and zinc oxides are also suitable as absorbers. Furthermore, absorbers having a solubility of at least 0.2 wt.-% and in particular at least 0.5 wt.-% in the composite resin composition are preferred.

o-Hydroxyphenylbenzotriazoles such as 2-(2H-benzotriazol-2-yl)-4-methylphenol, 2-(5-chloro-2H-benzotriazol-2-yl)-4-methyl-6-tert-butyl-phenol, 2-(5-chloro-2H-benzotriazol-2-yl)-4,6-di-tert-butyl-phenol, 2-(2H-benzotriazol-2-yl)-4,6-di-tert-pentyl-phenol, 2-(2H-benzotriazol-2-yl)-4-methyl-6-dodecyl-phenol, 2-(2H-benzotriazol-2-yl)-4,6-bis-(1-methyl-1-phenylethyl)-phenol, 2-(2H-benzotriazol-2-yl)-6-(1-methyl-1-phenylethyl)-4-(1,1,3,3-tetramethylbutyl)-phenol, 2-(2H-benzotriazol-2-yl)-4-(1,1,3,3-tetramethylbutyl)-phenol or 3-(2H-benzotriazol-2-yl)-5-tert-butyl-4-hydroxy-benzenepropanoic acid ester, o-hydroxyphenyltriazines such as 2-(2-hydroxy-4-hexyloxy-phenyl)-4,6-diphenyl-1,3,5-triazine or 2-(2-hydroxy-4-[2-hydroxy-3-dodecyloxy-propyloxy]-phenyl)-4,6-bis-(2,4-dimethylphenyl)-1,3,5-triazine, o-hydroxybenzophenones such as 2-hydroxy-4-octyloxy-benzophenone, cyanoacrylates such as ethyl-2-cyano-3,3-diphenylacrylate, 2-ethylhexyl-2-cyano-3,3-diphenylacrylate or tetrakis-[(2-cyano-3,3-diphenylacryloyl)oxymethyl]-methane, hindered amine light stabilizers (HALS) such as N,N'-bisformyl-N,N'-bis-(2,2,6,6-tetramethyl-4-piperidinyl)-hexamethylenediamine, bis-(2,2,6,6-tetramethyl-4-piperidyl)-sebacate, bis-(1,2,2,6,6-pentamethyl-4-piperidyl)-sebacate or methyl-(1,2,2,6,6-pentamethyl-4-piperidyl)-sebacate, salicylic acid esters as well as mixtures thereof are particularly suitable. o-Hydroxyphenylbenzotriazoles and in particular 2-(2H-benzotriazol-2-yl)-4-methyl-6-dodecylphenol are particularly preferred.

In this context, absorbers which scarcely absorb or do not absorb at all in the wavelength range of the second photopolymerization initiator are preferred according to the invention. Absorbers having a molar decadic absorption coefficient of less than 10 l/(mol·cm) in the wavelength range of from 400 to 750 nm and in particular in the wavelength range of from 420 to 750 nm and most preferably in the wavelength range of from 440 to 700 nm are particularly preferred.

In a particularly preferred embodiment, at least one phosphine oxide is used as first photopolymerization initiator, at least one α-diketone in combination with at least one amine accelerator is used as second photopolymerization initiator and at least one benzotriazole is used as absorber. A specific example is a combination of bis-(2,4,6-trimethylbenzoyl)-phenylphosphine oxide, camphorquinone with 4-(N,N-dimethylamino)-benzoic acid diethyl ester and 2-(2H-benzotriazol-2-yl)-4-methyl-6-dodecylphenol.

In a further particularly preferred embodiment, at least one phosphine oxide is used as first photopolymerization initiator, a mixture of at least one acylgermanium compound with at least one α-diketone in combination with at least one amine accelerator is used as second photopolymerization initiator and at least one benzotriazole is used as absorber. A specific example is a combination of bis-(2,4,6-trimethylbenzoyl)-phenylphosphine oxide, bis-(4-methoxybenzoyl)-diethylgermanium, camphorquinone, 4-(N,N-dimethylamino)-benzoic acid diethyl ester and 2-(2H-benzotriazol-2-yl)-4-methyl-6-dodecylphenol.

The composite resin composition comprises at least one polyreactive binder. Binders based on radically polymerizable monomers and/or prepolymers are preferred.

Mono- or multifunctional (meth)acrylates or mixtures thereof are particularly suitable as radically polymerizable binders. By mono-functional (meth)acrylic compounds are meant compounds with one, by multifunctional (meth)acrylic compounds are meant compounds with two or more, preferably 2 to 3 polymerizable groups. Suitable examples are methyl-, ethyl-, 2-hydroxyethyl-, butyl-, benzyl-, tetrahydrofurfuryl- or isobornyl(meth)acrylate, p-cumyl-phenoxyethylene glycol methacrylate (CMP-1E), bisphenol-A-di(meth)acrylate, bis-GMA (an addition product of methacrylic acid and bisphenol-A-diglycidyl ether), ethoxylated or propoxylated bisphenol-A-dimethacrylate, such as e.g. the bisphenol-A-dimethacrylate SR-348c (Sartomer) with 3 ethoxy groups or 2,2-bis[4-(2-methacryloxy propoxy)-phenyl]propane, UDMA (an addition product of 2-hydroxyethyl methacrylate and 2,2,4-trimethyl-hexamethylene diisocyanate), di-, tri- or tetraethylene glycol di(meth)acrylate, trimethylolpropane tri(meth)acrylate, pentaerythritol tetra(meth)acrylate, as well as glycerin di- and trimethacrylate, 1,4-butanediol di(meth)acrylate, 1,10-decanediol di(meth)acrylate (D3MA) or 1,12-dodecanediol di-(meth)acrylate. Preferred (meth)acrylate monomers are benzyl-, tetrahydrofurfuryl- or isobornyl methacrylate, p-cumyl-phenoxyethylene glycol methacrylate, 2,2-bis[4-(2-methacryloxypropoxy)phenyl]propane, bis-GMA, UDMA, SR-348c and D3MA.

N-mono- or N-disubstituted acrylamides, such as e.g. N-ethylacrylamide or N,N-dimethacrylamide, or bisacrylamides, such as e.g. N,N'-diethyl-1,3-bis(acrylamido)propane, 1,3-bis(methacrylamido)-propane, 1,4-bis(acrylamido)butane or 1,4-bis(acryloyl)piperazine can also be used as radically polymerizable binders.

Furthermore, known low-shrinkage monomers capable of radical ring-opening polymerization, such as e.g. mono- or multifunctional vinylcyclopropanes or bicyclic cyclopropane derivatives (cf. DE 196 16 183 C2 or EP 1 413 569 A1) or cyclic allyl sulphides (cf. U.S. Pat. No. 6,043,361 or U.S. Pat. No. 6,344,556), can also be used as radically polymerizable binders, which can moreover also be used in combination with the above-listed di(meth)acrylate cross-linkers.

Moreover, radically polymerizable polysiloxanes, which can be produced from suitable methacryl silanes such as e.g. 3-(methacryloyloxy)-propyltrimethoxysilane and are described e.g. in DE 199 03 177 C2, can also be used as radically polymerizable binders.

Preferably, mixtures of the above-named monomers are used.

The composite resin composition used according to the invention furthermore preferably also comprises organic or inorganic filler particles to improve the mechanical properties or to adjust the viscosity. Preferred inorganic particulate fillers are amorphous spherical materials based on oxides such as $ZrO_2$ and $TiO_2$ or mixed oxides of $SiO_2$, $ZrO_2$ and/or $TiO_2$ having an average particle size of from 0.005 to 2 μm, preferably 0.1 to 1 μm, nanoparticulate or micro-fine fillers such as pyrogenic silica or precipitation silica having an average particle size of from 5 to 200 nm, preferably 10 to 100 nm, minifillers such as quartz, glass ceramic or glass powders having an average particle size of from 0.01 to 10 μm, preferably 0.1 to 1 μm, as well as X-ray-opaque fillers such as ytterbium trifluoride or nanoparticulate tantalum(V) oxide or barium sulphate having an average particle size of from 10 nm to 1000 nm, preferably 100 to 300 nm.

Moreover, the compositions used according to the invention can comprise further additives, in particular solvents such as water or ethanol or corresponding solvent mixtures as well as for example stabilizers, flavorings, dyes, microbiocidal active ingredients, fluoride ion-releasing additives, optical brighteners or plasticizers.

Particularly preferred are composite resin compositions which comprise the following components:
  (a) 5 to 90 wt.-%, in particular 10 to 40 wt.-% and particularly preferably 20 to 40 wt.-% polyreactive binder,
  (b) 0.01 to 5.0 wt.-%, in particular 0.1 to 3.0 wt.-% and particularly preferably 0.1 to 1.0 wt.-% first photopolymerization initiator,
  (c) 0.01 to 2.0 wt.-%, in particular 0.1 to 1.0 wt.-% and particularly preferably 0.1 to 0.5 wt.-% second photopolymerization initiator,
  (d) 0.001 to 3.0 wt.-%, in particular 0.1 to 2.0 wt.-% and particularly preferably 0.5 to 1.0 wt.-% absorber and
  (e) 5 to 90 wt.-%, in particular 40 to 90 wt.-% and particularly preferably 50 to 80 wt.-% filler,
in each case relative to the total mass of the composition.

Quite particularly preferred are composite resin compositions which comprise the following components:
  (a) 10 to 40 wt.-% polyreactive binder,
  (b) 0.1 to 3.0 wt.-% first photopolymerization initiator,
  (c) 0.1 to 1.0 wt.-% second photopolymerization initiator,
  (d) 0.1 to 2.0 wt.-% absorber and
  (e) 40 to 90 wt.-% filler,
in each case relative to the total mass of the composition.

The invention also relates to a process for the stereolithographic production of a dental shaped part wherein a composite resin composition as defined above is cured in layers by the local introduction of radiation to form a three-dimensional body.

In particular, the invention also relates to a process for the stereolithographic production of a dental shaped part, wherein
  (i) a composite resin composition as defined above is cured in layers by the local introduction of radiation the emission maximum of which is at a wavelength of less than 400 nm, to form a three-dimensional body, and
  (ii) the obtained three-dimensional body is further cured by the introduction of radiation the emission maximum of which is at a wavelength of at least 400 nm.

Usually in step (i) the polymerizable groups of the polyreactive binder are only partially reacted and thus the composite resin is only partially cured. Optionally, a cleaning of the obtained three-dimensional body can then be effected in which for example excess composite material is mechanically removed. Finally, the obtained three-dimensional body is further cured in step (ii).

Compared with the production of dental component parts made of composite materials by means of grinding techniques, the stereolithographic process according to the invention is characterized by high cost-effectiveness because the construction times, compared with the grinding times of blanks, can be kept very low and a parallel production is possible. In addition, unlike with ground blanks, only very little material is required for the construction process. A further advantage is that, with the stereolithographic process according to the invention, dental component parts such as inlays and onlays can be produced with much finer and more sharply defined surface structures such as occlusal surfaces and fissures, which cannot be obtained using grinding techniques.

Surprisingly, it was also shown that, as a result of the use of at least one second photopolymerization initiator as well as radiation having an emission maximum in the visible range during the further curing in step (ii) in accordance with the present invention, a full curing with optimum depth effect is achieved.

The longest-wavelength emission maximum of the radiation used in step (i) preferably is at a wavelength of less than 400 nm, in particular in the range of from 240 to less than 400 nm and most preferably in the range of from 320 to less than 400 nm. The longest-wavelength emission maximum of the radiation used in step (ii) preferably is at a wavelength of at least 400 nm, in particular in the range of from 400 to 600 nm and most preferably in the range of from 400 to 500 nm.

The further curing in step (ii) can be carried out for example in a light furnace (e.g. Lumamat®). Preferably a light intensity of at least 1 mW/cm$^2$, in particular at least 10 mW/cm$^2$ and particularly preferably at least 100 mW/cm$^2$ is used in this context.

The invention also relates to the use of a composite resin composition as defined above in a process according to the invention.

The further curing in step (ii) can also be carried out intraorally. This is particularly preferred according to the invention. It has the advantage that no additional hardening device or separate work step is required.

The invention therefore also relates to a composite resin composition as defined above for use in a process for dental restoration, wherein
  (i) a composite resin composition as defined above is cured in layers by the local introduction of radiation the emission maximum of which is at a wavelength of less than 400 nm to form a three-dimensional body, and
  (ii) the obtained three-dimensional body is introduced into the mouth of a patient and further cured by the introduction of radiation the emission maximum of which is at a wavelength of at least 400 nm.

Preferred embodiments with regard to the composite resin composition and the radiation used are as defined above.

The intraoral further curing can be carried out for example with a dental LED light source (e.g. Bluephase, Ivoclar Vivadent AG, absorption maximum 460 nm). Preferably, a light intensity of at least 1 mW/cm$^2$, in particular at least 10 mW/cm$^2$ and particularly preferably at least 100 mW/cm$^2$ is used in this context.

Particularly preferably in step (ii) initially a layer of a dental cement is applied to cement the dental component to the tooth, and this layer is cured as well during the further curing in step (ii). Due to the presence of not yet reacted polymerizable groups, in particular on the surface of the three-dimensional body, an optimum bonding of the composite to the cement can be achieved. This provides great security and is extremely user-friendly.

Such process is shown schematically in FIG. 1. Initially a three-dimensional body in the shape of a dental component, for example a crown, is produced by means of stereolithography by curing a composite resin composition in layers by the local introduction of radiation of a light source λ1 the emission maximum of which is at a wavelength of less than 400 nm to form the three-dimensional body (A). The thus-obtained three-dimensional body is then applied to a tooth together with a layer of a dental cement (B and C). Then, by the introduction of radiation of a light source λ2 the emission maximum of which is at a wavelength of at least 400 nm, the three-dimensional body is further cured and simultaneously cemented to the tooth by curing the dental cement (D).

The composite resin composition used according to the invention and the process according to the invention are particularly suitable for the stereolithographic production of three-dimensional bodies and dental component parts in the shape of inlays, onlays, crowns and bridges based on composite resins.

The invention is explained in more detail below by means of examples.

EXAMPLES

Example 1

Resins of the following compositions were prepared:

| Component | Resin A (comparison) wt.-% | Resin B wt.-% |
|---|---|---|
| UDMA[1] | 14.20 | 14.33 |
| Bis-GMA[2] | 14.70 | 13.84 |
| Decane-1,10-dioldimethacrylate | 7.35 | 7.17 |
| Camphorquinone | 0.09 | 0.09 |
| Amine accelerator[3] | 0.22 | 0.21 |
| Lucerin TPO | 0.15 | 0.15 |
| Ivocerin | 0.04 | 0.04 |
| Dispersing additive[4] | 0.25 | 0.24 |
| Inorganic filler mixture[5] | 63.00 | 61.43 |
| Tinuvin 571 | — | 2.50 |

[1]Addition product of 2-hydroxyethyl methacrylate and 2,2,4-trimethylhexamethylene diisocyanate
[2]Addition product of methacrylic acid and bisphenol-A-diglycidyl-ether
[3]4-Dimethylamino-benzoic acid ethyl ester
[4]Dispersing additive containing acid groups (Byk-Chemie)
[5]Mixture of pyrogenic silica, barium aluminium silicate glass powder and ytterbium fluoride in a weight ratio of 3:2:1

Figure 2:
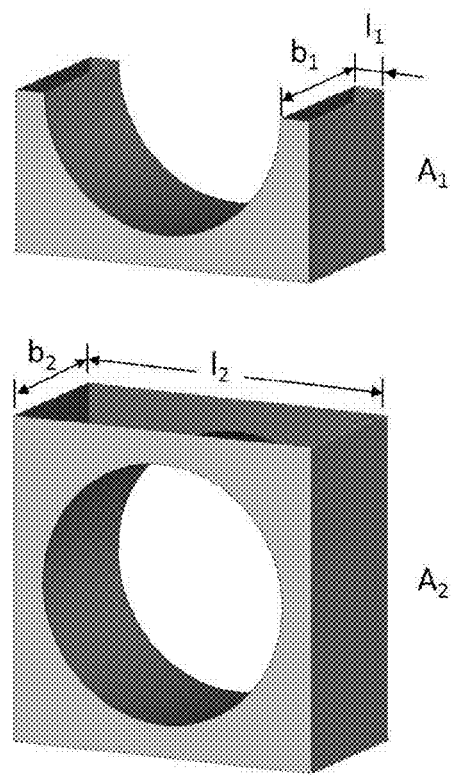
FIG. 2 shows the geometry of bodies produced in accordance with the invention.

Using the respective resins and radiation having a wavelength of 388 nm, bodies having the geometry shown in FIG. 2 were produced stereolithographically, wherein the nominal edge lengths were $l_1=1$ mm, $l_2=10$ mm and $b_1=b_2=5$ mm. To determine the geometric accuracy, the actual edge lengths of the bodies obtained were measured.

For the body produced from resin A, the absolute deviation from the nominal geometry on each edge was about 600 μm. The deviation of the surface $A_1=l_1*b_1$ was about 95%, and the deviation of the surface $A_2=l_2*b_2$ was about 38%.

In contrast to this, for the body produced from resin B according to the invention, the absolute deviation from the nominal geometry was no more than 90 μm on any edge. The deviation of the surface $A_1=l_1*b_1$ was only about 10%, and the deviation of the surface $A_2=l_2*b_2$ was only about 5%. This corresponds to an improvement of the geometric accuracy of about 90% and shows that by using the resin according to the invention an excellent geometric accuracy can be achieved.

Example 2

Using resin B from Example 1, 10 cylindrical test pieces (diameter 4 mm, height 4 mm) were produced stereolithographically, which were attached to small metal plates according to ISO 10477:2004 (D) using the adhesion system SR Link and the fixing composite Variolink 2 and exposed to light from above through the test piece by means of illumination with an LED light source Bluephase, Programm HiP (Ivoclar Vivadent AG) with light having a wavelength of 460 nm for 3×10 s. A curing of the fixing composite and a post-curing of the stereolithographically produced bodies were thereby achieved simultaneously. An average shear bond strength of 17.58 MPa was measured.

Example 3

A resin of the following composition was prepared:

| Component | wt.-% |
|---|---|
| Bis-GMA[1] | 15.26 |
| UDMA[2] | 14.43 |
| Decane-1,10-dioldimethacrylate | 7.07 |
| Camphorquinone | 0.09 |
| Amine accelerator[3] | 0.21 |
| Lucerin TPO | 0.14 |
| Chromophoric pigments | 0.43 |
| Inhibitor | 0.03 |
| Inorganic filler mixture[4] | 62.04 |
| Tinuvin 571 | 0.30 |

[1]Addition product of methacrylic acid and bisphenol-A-diglycidyl-ether
[2]Addition product of 2-hydroxyethyl methacrylate and 2,2,4-trimethylhexamethylene diisocyanate
[3]4-Dimethylamino-benzoic acid ethyl ester
[4]Mixture of pyrogenic silica, barium aluminium silicate glass powder and ytterbium fluoride in a weight ratio of 3:2:1

Using this resin and radiation having a wavelength of 388 nm, 10 test pieces (width 2 mm, length 2 mm, height 25 mm) were produced stereolithographically. The 3-point bending strength and the bending E modulus of the thus-obtained bodies were determined according to the ISO Standard ISO-4049 (Dentistry—Polymer-based filling, restorative and luting materials). An average bending strength of 62.4 MPa and an average E modulus of 1695 N/mm$^2$ were measured.

Following the stereolithographic construction process, 10 further test pieces produced in the same way were post-hardened on one side using an LED light source Bluephase, Programm HiP (Ivoclar Vivadent AG) with light having a wavelength of 460 nm for 3×10 s. An average bending strength of 84.2 MPa and an average E modulus of 2466 N/mm$^2$ were measured.

The invention claimed is:

1. A process for producing a dental shaped part, which process comprises curing a composite resin composition comprising
    (a) at least one polyreactive binder,
    (b) a first photopolymerization initiator having an absorption maximum at a wavelength of less than 400 nm,
    (c) a second photopolymerization initiator having an absorption maximum at a wavelength of at least 400 nm and
    (d) an absorber having an absorption maximum at a wavelength of less than 400 nm,
    by means of stereolithography, wherein
    (i) the composite resin composition is cured in layers by the local introduction of radiation the emission maximum of which is at a wavelength of less than 400 nm to form a three-dimensional body, and
    (ii) the obtained three-dimensional body is further cured by the introduction of radiation the emission maximum of which is at a wavelength of at least 400 nm.

2. The process according to claim 1, wherein the longest-wavelength absorption maximum of the first photopolymerization initiator is at a wavelength of less than 400 nm.

3. The process according to claim 1, wherein the longest-wavelength absorption maximum of the first photopolymerization initiator is at a wavelength in the range of from 360 to less than 400 nm.

4. The process according to claim 1, wherein the longest-wavelength absorption maximum of the second photopolymerization initiator is at a wavelength of at least 400 nm.

5. The process according to claim 1, wherein the longest-wavelength absorption maximum of the second photopolymerization initiator is at a wavelength in the range of from 400 to 500 nm.

6. The process according to claim 1, wherein the longest-wavelength absorption maximum of the absorber is at a wavelength of less than 400 nm.

7. The process according to claim 1, wherein the longest-wavelength absorption maximum of the absorber is at a wavelength in the range of from 330 to less than 400 nm.

8. The process according to claim 1, wherein the difference between the absorption maxima of the first and second photopolymerization initiators is at least 5 nm.

9. The process according to claim 1, wherein the composition comprises a first photopolymerization initiator selected from the group consisting of phosphine oxides, benzoins, benzil ketals, acetophenones, benzophenones, thioxanthones as well as mixtures thereof.

10. The process according to claim 1, wherein the composition comprises a second photopolymerization initiator selected from the group consisting of α-diketones, acylgermanium compounds, metallocenes as well as mixtures thereof.

11. The process according to claim 10, wherein the second photopolymerization initiator is selected from the group consisting of α-diketones consisting of camphorquinone, 1-phenyl-propane-1,2-dione as well as mixtures thereof, and optionally an amine accelerator selected from the group consisting of p-(dimethylamino)-benzoic acid ethyl ester, dimethylaminoethyl methacrylate, N,N-dimethylaniline, N,N-dimethyl-p-toluidine, triethanolamine and mixtures thereof.

12. The process according to claim 10, wherein the second photopolymerization initiator is selected from the group consisting of monoacyltrialkyl- and diacyldialkylgermanium compounds as well as mixtures thereof.

13. The process according to claim 1, wherein the composition comprises an absorber selected from the group consisting of benzotriazoles, triazines, benzophenones, cyanoacrylates, salicylic acid derivatives, hindered amine light stabilizers (HALS), inorganic salts as well as mixtures thereof.

14. The process according to claim 1, wherein the at least one polyreactive binder is selected from radically polymerizable monomers and prepolymers.

15. The process according to claim 1, wherein the at least one polyreactive binder is selected from mono- and multifunctional (meth)acrylates and their mixtures.

16. The process according to claim 1, wherein the composition further comprises filler.

17. The process according to claim 1, wherein the composition comprises
 (a) 5 to 90 wt.-% polyreactive binder,
 (b) 0.01 to 5.0 wt.-% first photopolymerization initiator,
 (c) 0.01 to 2.0 wt.-% second photopolymerization initiator,
 (d) 0.001 to 3.0 wt.-% absorber and
 (e) 5 to 90 wt.-% filler,
 in each case relative to the total mass of the composition.

18. The process according to claim 1, wherein the dental shaped part has the shape of an inlay, onlay, a crown or a bridge.

19. The process according to claim 1, wherein
 (i) the composite resin composition is cured in layers by the local introduction of radiation the emission maximum of which is at a wavelength of less than 400 nm to form a three-dimensional body, and
 (ii) the obtained three-dimensional body is introduced into the mouth of a patient and further cured by the introduction of radiation the emission maximum of which is at a wavelength of at least 400 nm.

20. The process according to claim 19, wherein in step (ii) initially a layer of a dental cement is applied to cement the dental component to the tooth, and this layer is also cured during the further curing in step (ii).

21. The process according to claim 19, wherein the three-dimensional body has the shape of an inlay, onlay, a crown or a bridge.

22. The process according to claim 2, wherein the longest-wavelength absorption maximum of the first photopolymerization initiator is at a wavelength in the range of from 300 to less than 400 nm.

23. The process according to claim 2, wherein the longest-wavelength absorption maximum of the first photopolymerization initiator is at a wavelength in the range of from 330 to less than 400 nm.

24. The process according to claim 2, wherein the longest-wavelength absorption maximum of the first photopolymerization initiator is at a wavelength in the range of 345 to less than 400 nm.

25. The process according to claim 4, wherein the longest-wavelength absorption maximum of the second photopolymerization initiator is at a wavelength in the range of from 400 to 600 nm.

26. The process according to claim 5, wherein the longest-wavelength absorption maximum of the second photopolymerization initiator is at a wavelength in the range of from 420 to 480 nm.

27. The process according to claim 6, wherein the longest-wavelength absorption maximum of the absorber is at a wavelength in the range of from 300 to less than 400 nm.

28. The process according to claim 7, wherein the longest-wavelength absorption maximum of the absorber is at a wavelength in the range of from 345 to less than 400 nm.

29. The process according to claim 7, wherein the longest-wavelength absorption maximum of the absorber is at a wavelength in the range of from 360 to less than 400 nm.

30. The process according to claim 8, wherein the difference between the absorption maxima of the first and second photopolymerization initiators is at least 10 nm.

31. The process according to claim 8, wherein the difference between the absorption maxima of the first and second photopolymerization initiators is at least 15 nm.

32. The process according to claim 9, wherein the first photopolymerization initiator is selected from the group consisting of acyl- and bisacylphosphine oxides, benzoin, benzoin alkyl ethers, benzil dialkyl ketals, α-hydroxyacetophenones, α-dialkoxyacetophenones, α-aminoacetophenones, alkyl¬ thioxanthones as well as mixtures thereof.

33. The process according to claim 9, wherein the first photopolymerization initiator is selected from the group consisting of 2,4,6-trimethyHbenzoyl diphenylphosphine oxide and bis-(2,4,6-trimethylbenzoyl)phenylphosphine oxide as well as mixtures thereof.

34. The process according to claim 10, wherein the second photopolymerization initiator is selected from the group consisting of α-diketones, monoacyl- and diacylgermanium compounds, titanocenes as well as mixtures thereof.

35. The process according to claim 12, wherein the second photopolymerization initiator is selected from the group consisting of benzoyltrimethylgermanium, dibenzoyldiethylgermanium, bis-(4-methoxybenzoyl)-diethylgermanium as well as mixtures thereof.

36. The process according to claim 13, wherein the absorber is selected from the group consisting of o-hydroxyphenylbenzotriazoles, o-hydroxyphenyltriazines, o-hydroxybenzophenones, cyanoacrylates, hindered amine light stabilizers (HALS), salicylic acid esters, nanoscale titanium dioxides and zinc oxides as well as mixtures thereof.

37. The process according to claim 13, wherein the absorber comprises 2-(2H-benzotriazol-2-yl)-4-methyl-6-dodecylphenol.

* * * * *